(12) United States Patent
Arai et al.

(10) Patent No.: US 8,226,560 B2
(45) Date of Patent: Jul. 24, 2012

(54) REFERENCE IMAGE DISPLAY METHOD FOR ULTRASONOGRAPHY AND ULTRASONIC DIAGNOSIS APPARATUS

(75) Inventors: Osamu Arai, Ibaraki (JP); Takao Iwasaki, Miyagi (JP); Tsuyoshi Mitake, Chiba (JP); Koichi Oshio, Tokyo (JP); Kiyoshi Okuma, Tokyo (JP); Hiroshi Shinmoto, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 1464 days.

(21) Appl. No.: 10/556,032

(22) PCT Filed: May 10, 2004

(86) PCT No.: PCT/JP2004/006238
§ 371 (c)(1),
(2), (4) Date: Nov. 8, 2005

(87) PCT Pub. No.: WO2004/098414
PCT Pub. Date: Nov. 18, 2004

(65) Prior Publication Data
US 2007/0010743 A1    Jan. 11, 2007

(30) Foreign Application Priority Data

May 8, 2003 (JP) .................................. 2003-130490
May 8, 2003 (JP) .................................. 2003-130600

(51) Int. Cl.
*A61B 8/00* (2006.01)
*A61B 5/05* (2006.01)
(52) U.S. Cl. .................. 600/443; 600/407; 128/916
(58) Field of Classification Search .................. 600/407, 600/117, 424–425, 427, 429, 439, 441, 443, 600/410, 414, 426, 444, 445, 446, 447; 345/419, 427; 128/916
See application file for complete search history.

(56) References Cited

U.S. PATENT DOCUMENTS 5,159,931 A * 11/1992 Pini .............................. 600/443
5,531,227 A * 7/1996 Schneider ..................... 600/425
(Continued)

FOREIGN PATENT DOCUMENTS

CN    1168625 A    12/1997
(Continued)

OTHER PUBLICATIONS

Comeau, Roch M., Intraoperative Ultrasound for Guidance and Tissue Shift Correction in Image-Guided Neurosurgery, Medical Physics, AIP, Melville, NY, vol. 27, No. 4, pp. 787-800, Apr. 1, 2000.
(Continued)

*Primary Examiner* — Francis Jaworski
(74) *Attorney, Agent, or Firm* — Antonelli, Terry, Stout & Kraus, LLP.

(57) ABSTRACT

An ultrasonic image 105, 106 is captured by an ultrasonic probe 104. A reference image 111 is obtained by extracting a tomographic image corresponding to the scan plane of the ultrasonic image from volume image data that is pre-obtained by a diagnostic imaging apparatus 102 and that is stored in a volume-data storing unit 107. The ultrasonic image and the reference image 111 are displayed on the same screen 114. In this case, of the reference image, a portion corresponding to the view area of the ultrasonic image is extracted and the resulting reference image having the same region as the ultrasonic image is displayed as a fan-shaped image.

12 Claims, 12 Drawing Sheets

U.S. PATENT DOCUMENTS

| | | | | |
|---|---|---|---|---|
| 5,608,849 | A | * | 3/1997 | King, Jr. .................. 345/419 |
| 5,638,819 | A | * | 6/1997 | Manwaring et al. ......... 600/424 |
| 5,740,802 | A | * | 4/1998 | Nafis et al. ................. 600/407 |
| 5,841,830 | A | * | 11/1998 | Barni et al. ................. 378/15 |
| 6,077,226 | A | * | 6/2000 | Washburn et al. ........... 600/443 |
| 6,135,946 | A | * | 10/2000 | Konen et al. ................ 600/117 |
| 6,167,296 | A | * | 12/2000 | Shahidi ....................... 600/427 |
| 6,193,660 | B1 | * | 2/2001 | Jackson et al. .............. 600/443 |
| 6,290,648 | B1 | * | 9/2001 | Kamiyama ................... 600/443 |
| 6,346,940 | B1 | * | 2/2002 | Fukunaga .................... 345/427 |
| 6,442,417 | B1 | * | 8/2002 | Shahidi et al. ............... 600/429 |
| 6,443,894 | B1 | * | 9/2002 | Sumanaweera et al. ...... 600/443 |
| 6,458,082 | B1 | * | 10/2002 | Jackson et al. .............. 600/441 |
| 6,671,538 | B1 | * | 12/2003 | Ehnholm et al. ............. 600/425 |
| 6,681,129 | B2 | * | 1/2004 | Matsuzaki et al. ........... 600/407 |
| 6,685,644 | B2 | * | 2/2004 | Seo et al. ..................... 600/447 |
| 6,690,963 | B2 | * | 2/2004 | Ben-Haim et al. ........... 600/424 |
| 6,728,424 | B1 | * | 4/2004 | Zhu et al. ..................... 382/294 |
| 6,741,883 | B2 | * | 5/2004 | Gildenberg .................. 600/429 |
| 6,775,404 | B1 | * | 8/2004 | Pagoulatos et al. .......... 382/154 |
| 6,968,224 | B2 | * | 11/2005 | Kessman et al. ............. 600/407 |
| 6,990,368 | B2 | * | 1/2006 | Simon et al. ................. 600/425 |
| 7,103,205 | B2 | * | 9/2006 | Wang et al. .................. 382/132 |
| 7,127,090 | B2 | * | 10/2006 | Kreang-Arekul et al. .... 382/128 |
| 7,215,990 | B2 | * | 5/2007 | Feussner et al. ............. 600/424 |
| 7,570,791 | B2 | * | 8/2009 | Frank et al. .................. 382/132 |
| 2002/0156375 | A1 | | 10/2002 | Kessman et al. |
| 2003/0060706 | A1 | | 3/2003 | Sauer et al. |

FOREIGN PATENT DOCUMENTS

| | | |
|---|---|---|
| JP | 01-270861 A | 10/1989 |
| JP | 02-045038 A | 2/1990 |
| JP | 04-033651 A | 2/1992 |
| JP | 06-090927 A | 4/1994 |
| JP | 8-336531 A | 12/1996 |
| JP | 9-103434 A | 4/1997 |
| JP | 09-192106 A | 7/1997 |
| JP | 09-218939 A | 8/1997 |
| JP | 10-151131 | 6/1998 |
| JP | 2000-107185 | 4/2000 |
| JP | 2000-262511 A | 9/2000 |
| JP | 2000-308646 A | 11/2000 |
| JP | 2002-1112998 | 4/2002 |
| WO | WO 00/54689 | 9/2000 |
| WO | WO 00/57767 | 10/2000 |
| WO | WO 01/01845 A2 | 1/2001 |

OTHER PUBLICATIONS

Pagoulatos, N. et al. Interactive 3D Registration of Ultrasound and Magnetic Resonance Images Based on a Magnetic Position Sensor, IEEE Transactions on Information Technology in Biomedicine, IEEE Service Center, Los Alamitos, CA, vol. 3, No. 4., pp. 278-288, Dec. 31, 1999.

European Office Action dated Mar. 25, 2010, issued in corresponding European Patent Application No. 04 732 004.9.

Chinese Office Action issued in corresponding Chinese Patent Application No. 200810181246.8, dated Apr. 2, 2010.

Japanese Office Action, dated Feb. 8, 2011, issued in corresponding Japanese Patent Application No. 2008-188614.

Japanese Office Action, dated Feb. 15, 2011, issued in corresponding Japanese Patent Application No. 2008-188659.

Japanese Office Action issued in corresponding Japanese Patent Application No. JP 2011-017936, dated Sep. 13, 2011.

Japanese Office Action issued in corresponding Japanese Patent Application No. JP 2011-017942, dated Sep. 13, 2011.

Japanese Office Action (Decision of Rejection) issued in corresponding Japanese Patent Application No. JP 2011-017934, dated Sep. 20, 2011.

Decision of Rejection, dated Jan. 31, 2012, issued in corresponding Japanese Patent Application No. 2011-017936.

Decision to Dismiss an Amendment, dated Jan. 31, 2012, issued in corresponding Japanese Patent Application No. 2011-017936.

Decision of Rejection, dated Jan. 31, 2012, issued in corresponding Japanese Patent Application No. 2011-017942.

Decision to Dismiss an Amendment, dated Jan. 31, 2012, issued in corresponding Japanese Patent Application No. 2011-017942.

* cited by examiner

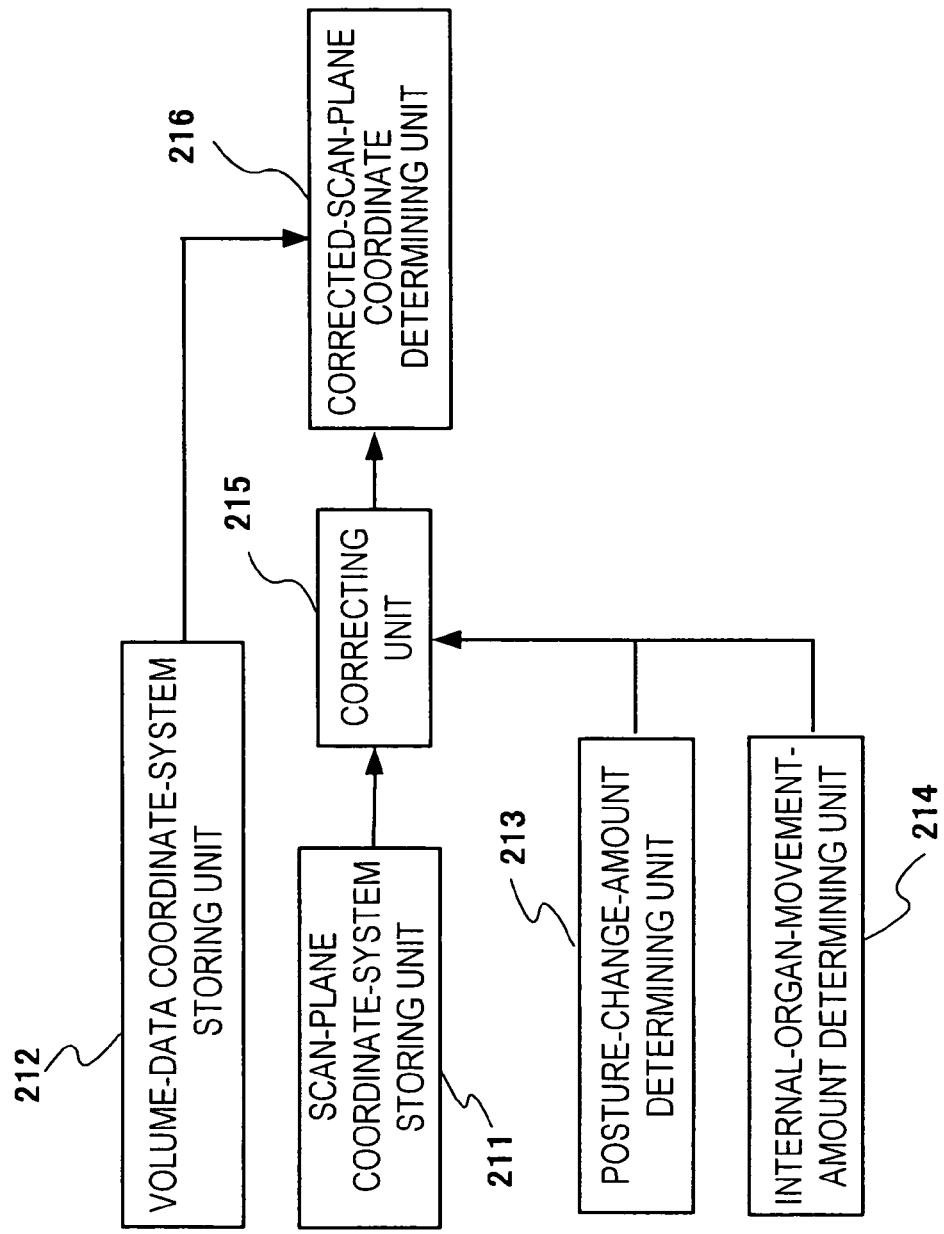

FIG. 11
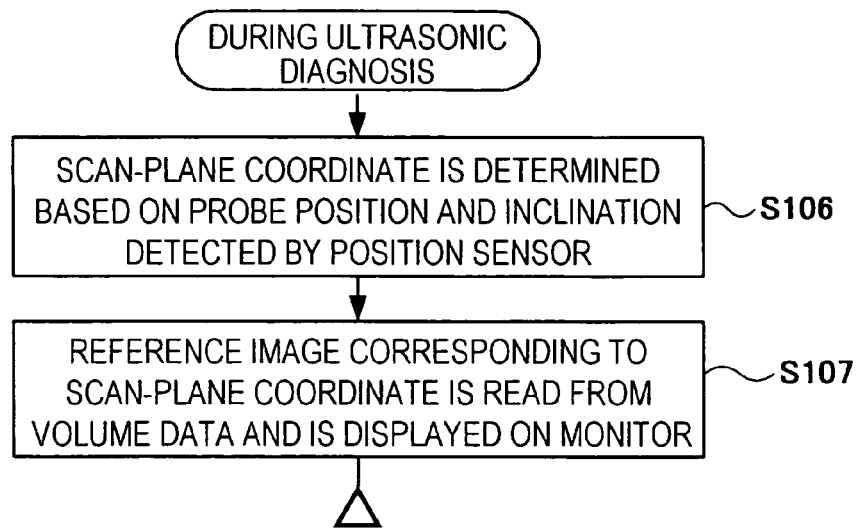
FIG. 12A
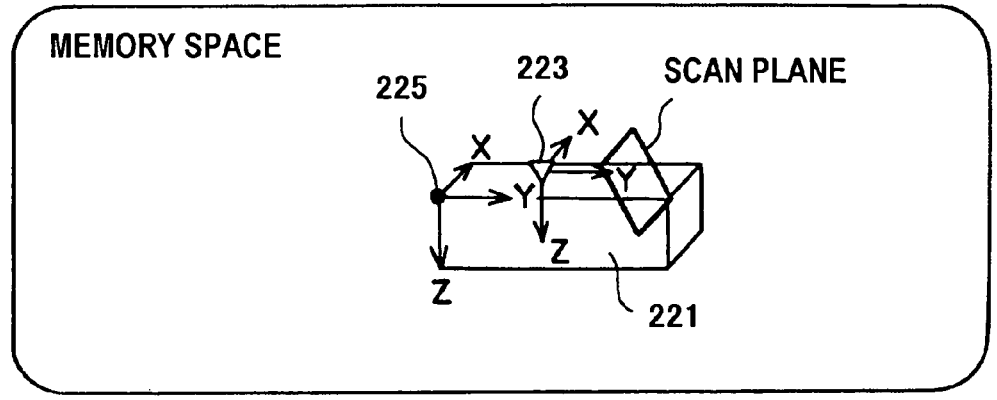
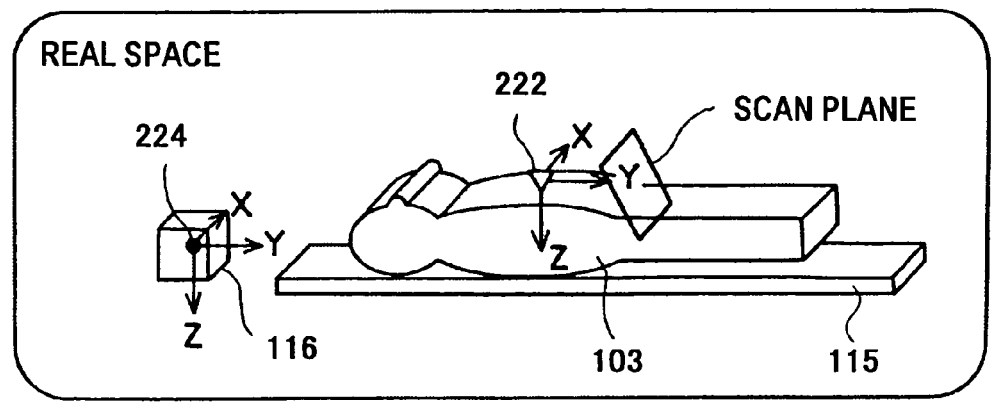
FIG. 12B

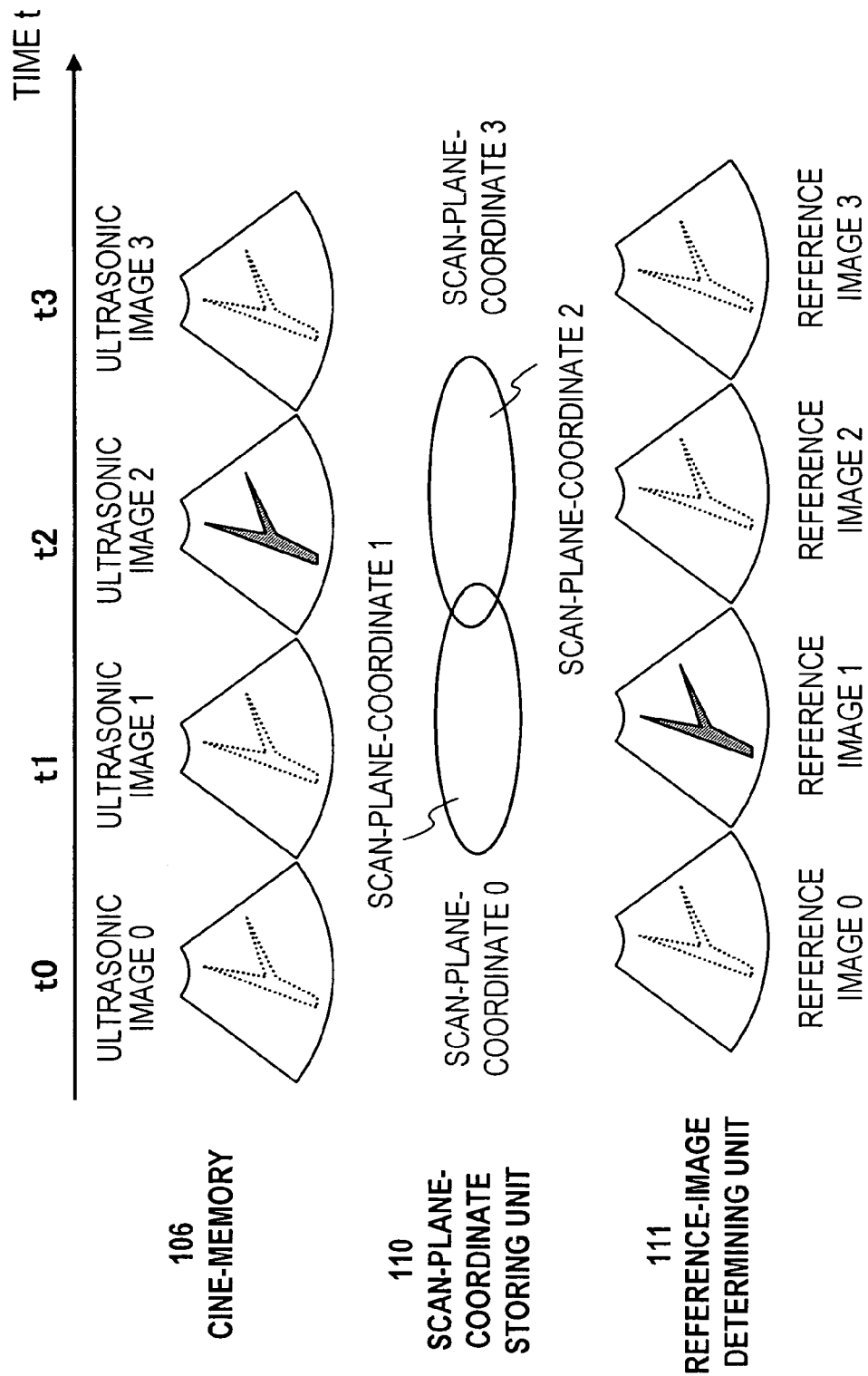

REFERENCE IMAGE DISPLAY METHOD FOR ULTRASONOGRAPHY AND ULTRASONIC DIAGNOSIS APPARATUS

TECHNICAL FIELD

The present invention relates to reference-image display methods for ultrasonography and ultrasonic diagnosis apparatuses using the methods. More specifically, the present invention relates to a technology preferably used for reconstructing, using multi-slice-image data of a patient obtained by a diagnostic imaging apparatus, a reference image of the same cross section as an ultrasonic scan plane in real time and for displaying the reference image and an ultrasonic image on the same screen. Examples of the diagnostic imaging apparatus include an ultrasonic diagnosis apparatus, a magnetic resonance imaging (MRI) apparatus, and an X-ray computed tomography (X-ray CT) apparatus.

BACKGROUND ART

Ultrasonic diagnosis apparatuses, which are one type of diagnostic imaging apparatuses, are frequently used for diagnosis, since they are easy to handle and are capable of performing noninvasive observation of arbitrary cross sections in real time. On the other hand, ultrasonic images captured by the ultrasonic diagnosis apparatuses are generally inferior in image quality to tomographic images captured by X-ray CT apparatuses or the like. Thus, comprehensive diagnosis may be performed while performing comparison with a tomographic image captured by another diagnostic imaging apparatus, such as an X-ray CT apparatus or an MRI apparatus (the tomographic image will hereinafter be referred to as a "reference image"). For example, when hepatophyma or the like is treated by radiofrequency ablation under the guidance of an ultrasonic image, it is conceived that a treatment portion is pre-located by CT diagnosis and a CT image thereof is used as a reference image to perform the guidance with the ultrasonic image.

However, when a CT image or MR image is merely rendered as the reference image, to recognize an association relationship between the images is a great burden on the operator. This is because the reference image provided by a CT image or MR image is typically a tomographic image of a cross section perpendicular to a body axis, whereas the ultrasonic image is a tomographic image of an arbitrary cross section specified by the operator.

Non-patent Document 1 describes an approach to facilitate the recognition of an association relationship between a reference image and an ultrasonic image. In the approach, a position sensor is attached to an ultrasonic probe to determine an ultrasonic scan plane and a reference image of the same cross section as the ultrasonic scan plane is reconstructed from multi-slice image data (hereinafter referred to as "volume image data") of a CT image or MR image and is rendered on a display screen. Similarly, Patent Document 1 also proposes a technology in which a reference image of the same cross section as an ultrasonic scan plane is reconstructed from the volume image data of a CT image or MR image and the reference image and an ultrasonic image are rendered on a display screen in an aligned or superimposed manner or in an alternately switched manner.

Patent Document 2 proposes a technology to aid manipulation for introducing a puncture needle into a body. That is, an ultrasonic scan plane is controlled so as to include the puncture needle and a reference image corresponding to the ultrasonic scan plane is cut out and is displayed. In the technology, two markers are attached to a body surface at a position corresponding to a patient's diseased area, into which the puncture needle is to be inserted, to obtain the volume image data of a reference image. Further, an ultrasonic probe is provided with an introducing portion for the puncture needle, so that the position and the angle of the puncture needle relative to the probe is fixed, and a sensor for detecting the position and the angle of the probe is attached to the probe to determine the ultrasonic scan plane. In this manner, a coordinate system for the volume image data and a coordinate system for the ultrasonic scan plane are associated with each other and a reference image corresponding to the ultrasonic scan plane is cut out and is displayed.

Non-patent Document 1: "Radiology" RNSA issued in 1996, page 517, K. Oshio

Patent Document 1: Japanese Unexamined Patent Application Publication No. 10-151131

Patent Document 2: Japanese Unexamined Patent Application Publication No. 2002-112998

DISCLOSURE OF INVENTION

However, in the prior art, although a reference image of a cross section corresponding to the scan plane of an ultrasonic image is cut out and is displayed on the same screen, no consideration is given to a scheme for matching display regions and the magnifications of a reference image and an ultrasonic image. For example, an ultrasonic image is a fan-shaped image obtained by capturing one part of a living body of a patient, whereas a CT image or MR image is typically a circular image obtained by capturing the entire body of the patient. Thus, when the reference image and the ultrasonic image are merely displayed in an aligned manner, there is also a problem in that it is difficult to recognize an association relationship of portions he or she desires to observe.

In addition, in order to obtain an ultrasonic image of a region including a target (e.g., a diseased area) arbitrarily specified on a reference image by the operator, he or she must manipulate the ultrasonic probe to search the region including the target. However, in the prior art, there is a problem in that no consideration is given to a scheme for facilitating the recognition of the positional relationship between the current ultrasonic scan plane and the target.

Accordingly, a first object of the present invention is to facilitate the recognition of an association relationship between an ultrasonic image and a reference image which are displayed on the same screen, the reference image being obtained by another diagnosis apparatus.

A second object of the present invention is to facilitate the recognition of the positional relationship between a target specified on an arbitrary reference image by an operator and the current ultrasonic scan plane.

In order to achieve the first object, an ultrasonic diagnosis apparatus of the present invention includes ultrasonic image generating means for reconstructing an ultrasonic image from reflection echo signals output from an ultrasonic probe, storing means for storing volume image data pre-obtained by a diagnostic imaging apparatus; reference-image generating means for extracting tomographic image data corresponding to a scan plane of the ultrasonic wave from the volume image data stored in the storing means and reconstructing a reference image, controlling means for causing the reference image and the ultrasonic image to be displayed on a screen, and displaying means for displaying the reference image and the ultrasonic image. In accordance with the tomographic image data and a positional relationship between the ultrasonic probe and a patient, the reference-image generating means extracts tomographic image data of a portion corresponding to a view area of the ultrasonic image to generate the reference image.

Thus, according to the present invention, since the reference image of the same region corresponding to the fan-shaped view-area of the ultrasonic image is displayed as a fan-shaped image, it is possible to easily recognize an association relationship between both the images. In this case, it is preferable that, of the reference image, the region corresponding to the view area be displayed with the same magnification as the ultrasonic image, since the recognition of an association relationship between both the images is further facilitated. It is also preferable that, of the reference image, brightness of a portion out of the view area of the ultrasonic image be reduced to perform display. With this arrangement, it is possible to perform comparison and observation without losing information of the reference image.

Further, displaying an acoustic shadow of the ultrasonic image on the reference image in a simulated manner further facilitates the recognition of an association relationship between both the images. Also, the ultrasonic image and the reference image can be displayed on the screen in an aligned manner, but the configuration is not limited thereto. A composite image of the ultrasonic image and the reference image can be displayed on the screen. The composite image can be an image obtained by superimposing a transparent image of the reference image on the ultrasonic image. Also, the composite image can be a difference image between the reference image and the ultrasonic image.

It is preferable that the reference-image generating means change an image size of the reference image in accordance with a speed of movement of the ultrasonic probe. This makes it possible to display the reference image according to a quick movement of the ultrasonic image, thus enhancing the freedom of manipulating the probe during the comparison and observation.

In order to achieve the second object, the ultrasonic diagnosis apparatus of the present invention includes a 3D bodymark determining unit for determining a positional relationship between the scan plane and a target set in the volume image data to cause a direction and a distance of the target relative to the scan plane to be displayed on the screen.

Additionally, the ultrasonic diagnosis apparatus of the present invention may further include a cine-memory for storing the ultrasonic image reconstructed by the ultrasonic-image generating means, a position sensor for detecting a position and an inclination of the ultrasonic probe, scan-plane-coordinate determining means for determining scan-plane coordinates of the ultrasonic image in accordance with an output from the position sensor, and scan-plane-coordinate-system storing means for storing the determined scan-plane coordinates. The reference-image generating means reads the scan-plane coordinates of the ultrasonic image from the scan-plane-coordinate-system storing means, reads the tomographic-image data corresponding to the read scan-plane coordinates, and reconstructs the reference image. The image processing means reads the ultrasonic image from the cine-memory and causes the reference image corresponding to the read ultrasonic image, the reference image being output from the reference-image generating means, to be displayed. With this arrangement, since ultrasonic images are sequentially read from the cine-memory and displayed and reference images corresponding to the ultrasonic images are sequentially cut out and displayed, comparison and observation can be performed using moving images.

It is also preferable that the ultrasonic diagnosis further includes at least one of a posture sensor for detecting a change in the posture of the patient and a sensor for detecting breathing and further has correcting means for correcting the scan-plane coordinates in accordance with an amount of internal-organ movement caused by a posture change or the breathing of the patient during ultrasonic diagnosis. With this arrangement, a displacement between the reference-image coordinate system and the ultrasonic-image coordinate system, the displacement being resulting from internal-organ movement caused by the breathing or a posture change of the patient, can be corrected. Thus, the accuracy of comparison and observation of both the images can be improved.

In addition or instead, the configuration can be such that, after the scan plane of the ultrasonic probe is scanned and one of an ultrasonic image and a reference image which has a distinctive point is searched for and frozen, the ultrasonic probe is manipulated, an image that is other than the frozen ultrasonic image or reference image and that matches the frozen one of the images is displayed and frozen, and a coordinate difference between scan-plane coordinates for the frozen one of the images and the other image is determined, so that the scan plane coordinates can be corrected based on the determined coordinate difference.

Further, in addition to the above-described configuration, the ultrasonic diagnosis apparatus can include: a position sensor for detecting a position and an inclination of the ultrasonic probe in association with a reference coordinate system; scan-plane-coordinate determining means for determining scan-plane coordinates of an ultrasonic image captured by the ultrasonic probe in association with the reference coordinate system, in accordance with an output from the position sensor; reference-point inputting means for setting a reference point on a reference image displayed on the screen based on the volume image data obtained in association with the reference coordinate system; volume-data-coordinate determining means for determining coordinates of tomographic data of the volume image data associated with the scan-plane coordinates, by determining a coordinate relationship between the position of the ultrasonic probe and a region that corresponds to the reference point and that exists on an ultrasonic image obtained by bringing the ultrasonic probe in contact with a body surface of the patient; and volume-data-coordinate storing means for storing the tomographic-image-data coordinates determined by the volume-data-coordinate determining means. The reference-image reconstructing means can read the coordinates of the tomographic image data, associated with the scan-plane coordinates determined by the scan-plane-coordinate determining means, from the volume-data-coordinate storing means and can extract the reference image. With this arrangement, the reference point for aligning the coordinate systems can be set inside the body of the patient. Thus, compared to the prior art in which a reference point is set on the body surface, the freedom of setting the reference point is increased and thus the accuracy of comparison and observation can be further improved.

BRIEF DESCRIPTION OF THE DRAWINGS

FIG. 9 is a detailed block diagram of a scan-plane-coordinate determining unit and a scan-plane-coordinate storing unit in the embodiment shown in FIG. 2.

FIG. 11 is a flow chart of embodiment of a reference-image display processing, during ultrasonic diagnosis, in the embodiment shown in FIG. 6.

FIG. 12 are diagrams illustrating an association relationship between volume image data and a scan-plane coordinate system.

FIG. 15 is a view illustrating a method for correcting a coordinate-system displacement resulting from internal-organ movement caused by the breathing of the patient.

BEST MODE FOR CARRYING OUT THE INVENTION

Preferred embodiments of the present invention will be described below with reference to the accompanying drawings.

(First Embodiment)

Figure 1:
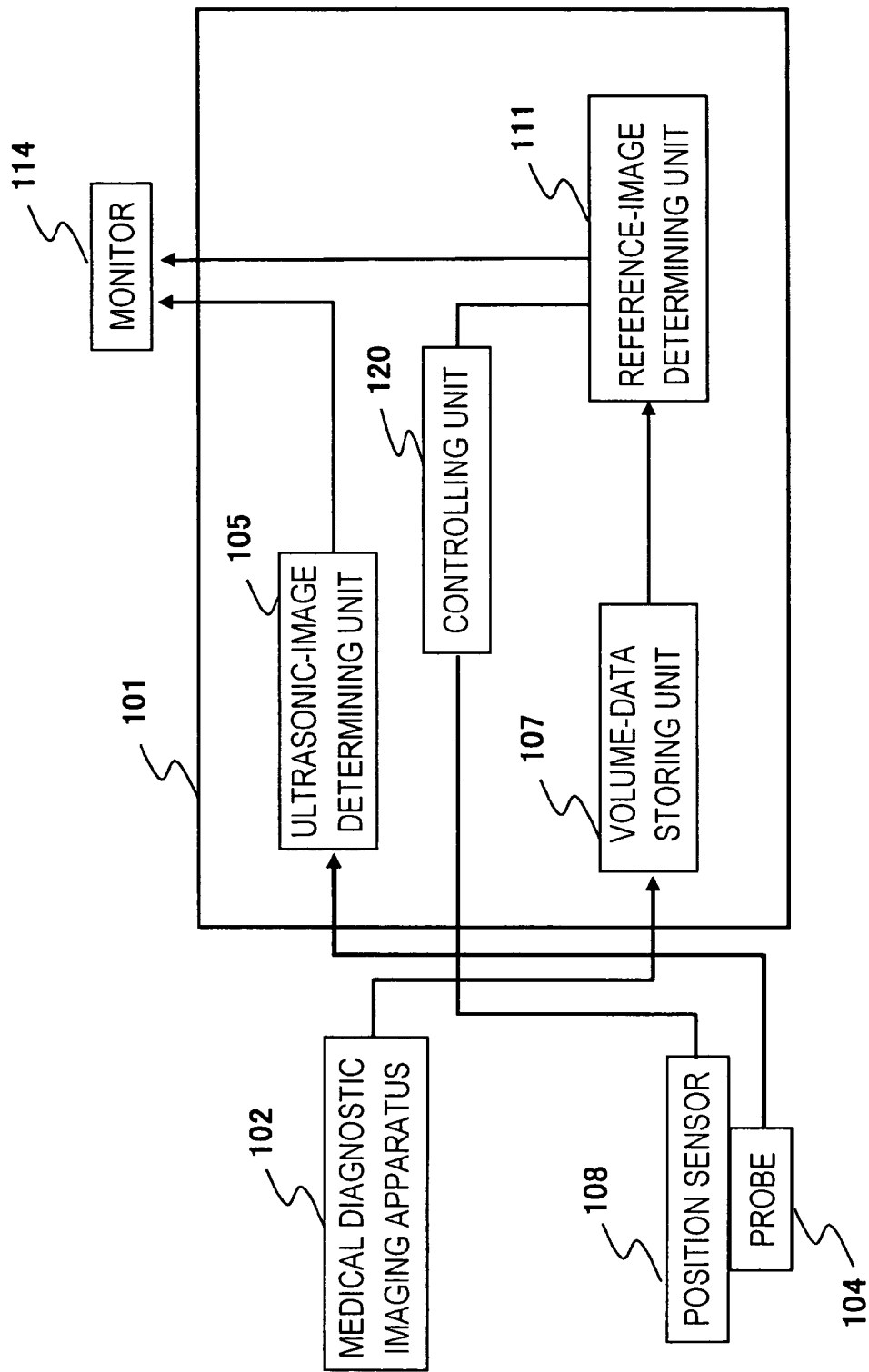
FIG. 1 is a block diagram of a basic diagnostic imaging system to which an ultrasonic diagnosis apparatus of one embodiment of the present invention is applied.

FIG. 1 is block diagram of a basic diagnostic imaging system to which an ultrasonic diagnosis apparatus of one embodiment of the present invention is applied. As shown, the diagnostic imaging system includes an ultrasonic diagnosis apparatus 101 according to one embodiment of the present invention and a medical diagnostic imaging apparatus 102 for obtaining volume image data that provides as a reference image. The volume image data refers to the data of multi-slice images obtained by capturing the inside of the body of a patient along multiple slice planes. The data of the volume images captured by the medical diagnostic imaging apparatus 102 is input to the ultrasonic diagnosis apparatus 101. A computed tomography apparatus (X-ray CT apparatus) or a magnetic resonance imaging apparatus (MRI apparatus) can be used as the medical diagnostic imaging apparatus 102. CT images and MR images have higher image qualities than ultrasonic images, as is known, and thus are suitable as reference images for ultrasonic images, which are inferior in image quality. However, when a temporal change in tissues of a patient is diagnosed with ultrasonic waves, the volume image data of a pre-obtained ultrasonic image can be drawn as the reference image.

In FIG. 1, descriptions of functions commonly included in the ultrasonic diagnosis apparatus 101 are omitted to avoid complexity, and only the functions of major units associated with displaying the reference image according to a feature of the present invention are described. As shown, the ultrasonic diagnosis apparatus 101 can broadly be divided into a section for reconstructing an ultrasonic image and a section for reconstructing the reference image. The former ultrasonic-image reconstructing section has a probe 104 and an ultrasonic-image determining unit 105. The latter reference-image reconstructing section has a volume-data storing unit 107 and a reference-image determining unit 111.

The ultrasonic-image determining unit 105 provides ultrasonic-image generating means for reconstructing an ultrasonic image in accordance with a reflection echo signal output from the probe 104. The ultrasonic-image determining unit 105 is adapted to associate signals output from a position sensor 108 with the reconstructed ultrasonic image. On the other hand, a controlling unit 120 is adapted to determine the scan-plane coordinates of the probe 104 in accordance with signals output from the position sensor 108 and to output the determined scan-plane coordinates to the reference-image determining unit 111. The reference-image determining unit 111 provides a reference-image generating means for extracting tomographic image data, corresponding to the scan-plane coordinates input from the controlling unit 120, from the volume-data storing unit 107 and reconstructing the reference image. Thus, the ultrasonic image reconstructed by the ultrasonic-image determining unit 105 and the reference image reconstructed by the reference-image determining unit 111 are adapted to be displayed on a monitor 114.

In particular, the reference-image determining unit 111 is configured such that it extracts tomographic-image data of a region corresponding to the view area of an ultrasonic image, in accordance with the scan-plane coordinates that are input from the controlling unit 120 and that are based on the positional relationship between the probe 114 and the patient, and generates a reference image.

According to the present embodiment configured as described above and shown in FIG. 1, a reference image corresponding to the fan-shaped view area of an ultrasonic image, the reference image and the ultrasonic image captured from the same region, is displayed as a fan-shaped image. This makes it possible to easily recognize an association relationship between both the images. In this case, displaying, of the reference image, a region corresponding to the view area of the ultrasonic image with the same magnification as the ultrasonic image can further facilitate the recognition of an association relationship between both the images. Also, displaying, of the reference image, a region that is out of the view area of the ultrasonic image, with reduced brightness, allows comparison and observation without loosing the information of the reference image.

(Second Embodiment)

Figure 2:
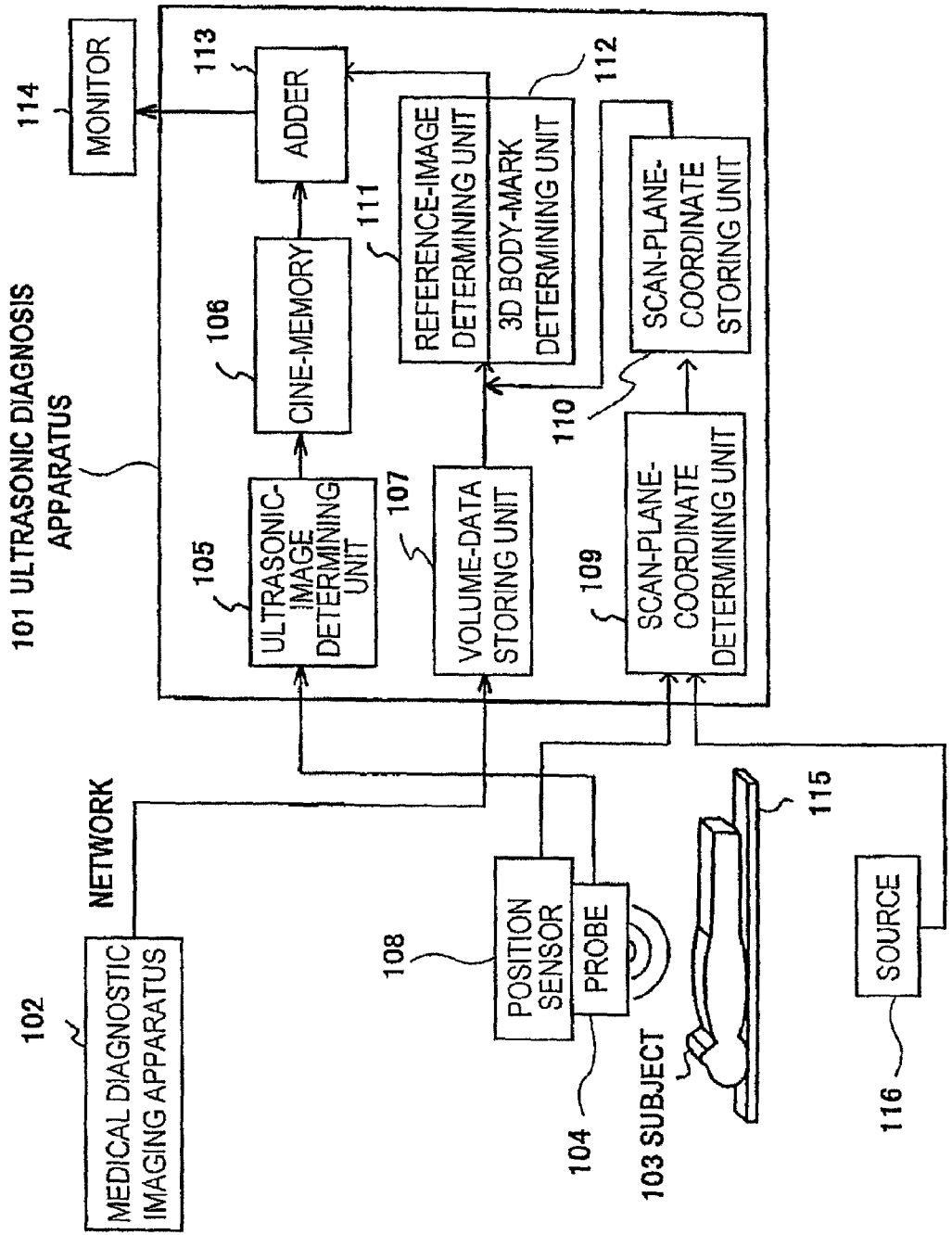
FIG. 2 is a block diagram of a specific diagnostic imaging system to which an ultrasonic diagnosis apparatus of another embodiment of the present invention is applied.

FIG. 2 shows the configuration of a specific diagnostic imaging system to which an ultrasonic diagnosis apparatus of the present invention is applied. In the figure, means having the same functional configurations as those in FIG. 1 are denoted with the same reference numerals and the descriptions thereof are omitted. In FIG. 2, a scan-plane-coordinate determining unit 109 and a scan-plane-coordinate storing unit 110 correspond to the configuration of the major unit of the controlling unit 120. A cine-memory 106 stores an ultrasonic image reconstructed by the ultrasonic-image determining unit 105. A 3D body-mark determining unit 112 is provided in connection with the reference-image determining unit 111. An adder 113 is configured as image processing means for appropriately combining images generated by the cine-memory 106, the reference-image determining unit 111, and the 3D body-mark determining unit 112. The monitor 114 is adapted to display images generated by the cine-memory 106, the reference-image determining unit 111, and the 3D body-mark determining unit 112 and the image processed by the adder 113.

Figure 3:
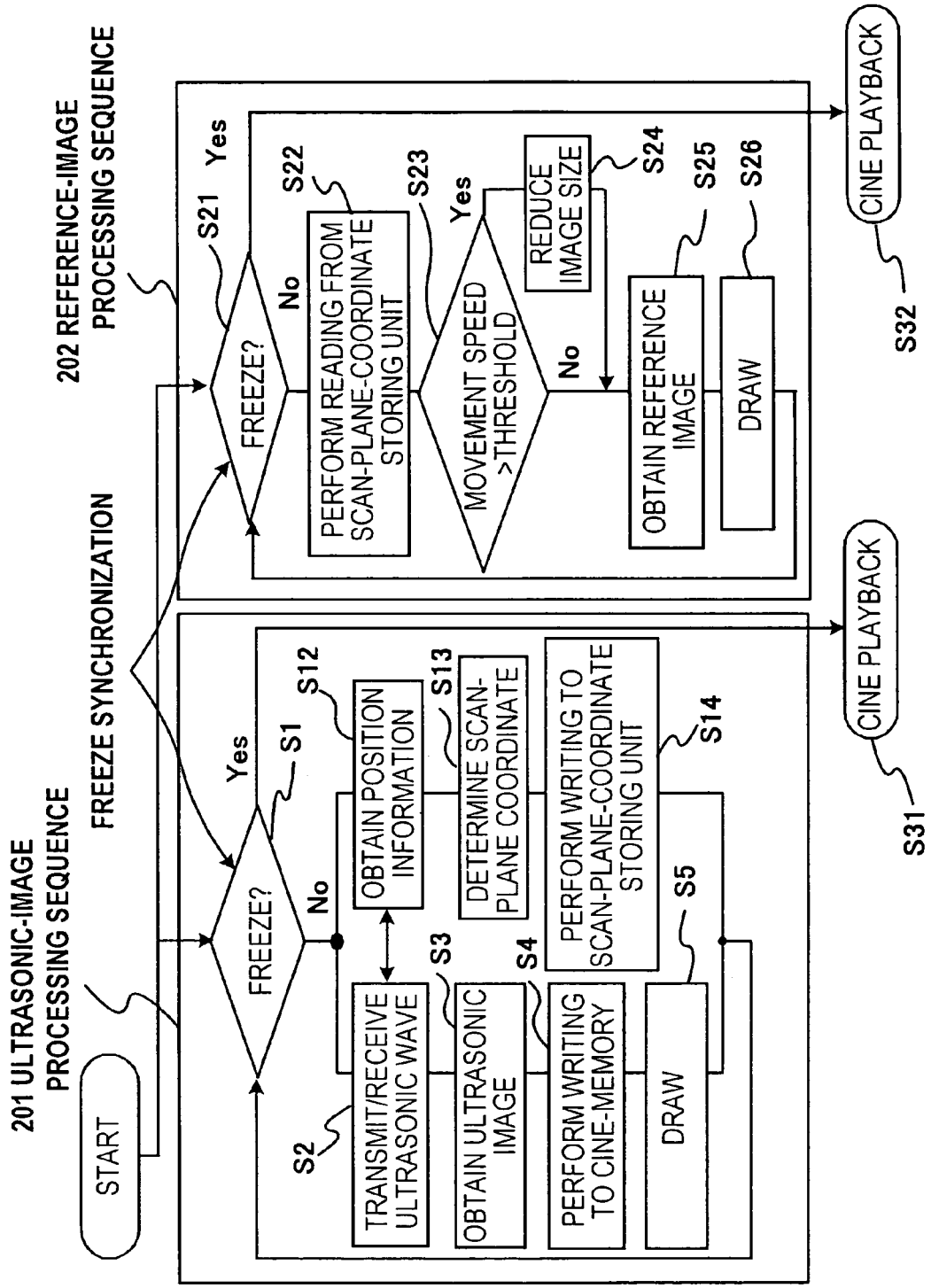
FIG. 3 is a flow chart showing a sequence of a drawing procedure for an ultrasonic image and a reference image in one embodiment of the present invention.

The probe 104 transmits/receives ultrasonic waves to/from a patient 103 and has built-in multiple transducers that generate ultrasonic waves and that receive reflection echoes. The ultrasonic-image determining unit 105 receives reflection echo signals output from the probe 104 and converts the received signals into digital signals to create an ultrasonic image 302, such as a tomographic image (B-mode image) or a color flow mapping image (CFM image), of a diagnosis region, as shown in FIG. 3 and so on. The cine-memory 106 receives ultrasonic images created by the ultrasonic-image determining unit 105 and stores ultrasonic images for multiple frames.

The volume-data storing unit 107 receives the volume image data of a reference image, captured by the medical diagnostic imaging apparatus 102, through a network or via a portable storage (MO) medium, such as a magneto-optical disk, and stores the volume image data in the ultrasonic diagnosis apparatus 101.

The position sensor 108 is attached to the probe 104 to detect the three-dimensional position and inclination of the probe. A source 116 for a coordinate system including the patient 103 is placed in the vicinity of a bed 115 on which the patient 103 lies. The principle of detecting the three-dimensional position and inclination of the probe 104 is that magnetic signals generated in a three-dimensional space by the source 116 is detected by the position sensor 108 and the three-dimensional position and inclination in a reference coordinate system formed by the source 116 are detected. A position sensor system, constituted by the position sensor 108 and the source 116, is not only limited to a magnet-based system but also may employ, for example, a known position sensor system, such as a system utilizing light.

In accordance with signals output from the position sensor 108 and the source 116, the scan-plane-coordinate determining unit 109 obtains the position and inclination information of the probe 104 in the reference coordinate system to determine scan-plane coordinates including the position and the inclination of a ultrasonic scan plane relative to the patient 103. The scan-plane-coordinate determining unit 109 is also adapted to calculate scan-plane coordinates in a reference-image coordinate system, in accordance with the determined scan-plane coordinates. That is, the scan-plane-coordinate determining unit 109 is adapted to determine scan-plane coordinate data including, for example, x, y, and z coordinate data of one corner of a scan plane and rotation angles about x, y, and y axes of the scan plane in a volume-image-data coordinate system. The scan-plane-coordinate data determined by the scan-plane-coordinate determining unit 109 is input to the scan-plane-coordinate storing unit 110 and scan plane coordinates for multiple frames are stored therein. In this case, it is preferable that the number of frames for scan plane coordinates stored be substantially the same as the number of frames of ultrasonic images captured in real time and stored in the cine-memory 106. The reference-image determining unit 111 provides reference-image reconstructing means, and receives scan-plane coordinate data and reconstructs a reference image of the same cross section as an ultrasonic scan image.

Next, a detailed configuration of the ultrasonic diagnosis apparatus 101 according to the present embodiment will be described in conjunction with the operation thereof. FIG. 3 is a flow chart for rendering an ultrasonic image and a reference image of the same cross section. The drawing processing is broadly classified into an ultrasonic-image processing sequence 201 for rendering an ultrasonic image and storing the scan-plane coordinates in a storage unit and a reference-image processing sequence 202. These two sequences 201 and 202 are executed in such a manner that starts and freezes are synchronized.

First, when an operator starts the two sequences 201 and 202, a determination is made as to whether a freeze instruction is input (S1). When freeze is not performed, the ultrasonic-image processing sequence 201 drives the probe 104 to transmit/receive ultrasonic waves to/from the patient 103 (S2). The ultrasonic-image determining unit 105 reconstructs an ultrasonic image in accordance with the reflection echo signals output from the probe 104 (S3). The reconstructed ultrasonic image is stored in the cine-memory 106 (S4) and is drawn on the monitor 114 (S5).

At this point, the position sensor 108 obtains the position and inclination of the probe 104 in synchronization with the transmission/reception of the ultrasonic waves (S12). In accordance with the position and inclination information input from the position sensor 108, the scan-plane-coordinate determining unit 109 determines scan-plane coordinates (S13). The determined scan-plane coordinates are sequentially written to the scan-plane-coordinate storing unit 110 (S14). In this case, the processing of steps S1 to S5 in the ultrasonic-image processing sequence 201 and the processing of steps S12 to S14 are executed in synchronization with each other.

On the other hand, in the reference-image processing sequence 202, a determination about freezing is made (S21). When freezing is not performed, scan-plane coordinates are read from the scan-plane-coordinate storing unit 110 (S22). Based on volume image data, the reference-image determining unit 111 reconstructs a reference image of the same cross section as the ultrasonic image (S25). The reconstructed reference image is drawn on the monitor 114 (S26). The processing of steps S23 and S24 will be described below.

Next, when the operator inputs an instruction for freezing the processing, the ultrasonic-image processing sequence 201 and the reference-image processing sequence 202 are adapted to execute cine playbacks in S31 and S32, respectively, based on the determination in steps S1 and S21. The cine playback of an ultrasonic image is executed by referring to the ultrasonic image data stored in the cine-memory 106. In contrast, the cine playback of a reference image is executed by using the scan-plane coordinate data stored in the scan-plane-coordinate storing unit 110 and by reconstructing a reference image corresponding to the scan plane based on the volume image data. The ultrasonic image data stored in the cine-memory 106 and the scan-plane coordinate data stored in the scan-plane-coordinate storing unit 110 are stored in synchronization with each other, it is possible to render an ultrasonic image and a reference image whose time phases are the same. The cine playback of an ultrasonic image is performed by referring to the ultrasonic-image data stored in the cine-memory 106, whereas the cine-playback of a reference image is performed by referring to the scan-plane-coordinate data stored in the scan-plane-coordinate storing unit 110. Thus, it is sufficient for the memory of the scan-plane-coordinate storing unit 110 to store only scan-plane-coordinate data, the memory capacity can be reduced. Similarly, for storing a moving image, merely storing scan-plane coordinates corresponding to volume image data makes it possible to play back the moving picture while reconstructing it from the volume image data. Thus, a moving-image file having a small file size can be created.

Now, an image-display processing method according to a feature of the present invention will be described with reference to FIG. 4. First, in accordance with the enlargement factor (magnification) of the ultrasonic image 302, the reference-image determining unit 111 enlarges or reduces a reference image and displays it at the same magnification, as shown in a reference image 301 shown in FIG. 4. The reference-image determining unit 111 also extracts an out-of-view area 312 corresponding to a fan-shaped viewing angle 311 of the ultrasonic image 302 and reduces the brightness of a reference image corresponding to the region 312. As a result, the reference image is displayed in the same display format and with the same magnification as those of the ultrasonic image 302, thus making it easy to recognize an association relationship between the ultrasonic image 302 and the reference image. This arrangement also makes it possible to perform display without losing the information of a reference image in the out-of-view area of the ultrasonic image. Also, an acoustic shadow 307, such as a bone 313 (or air), appears on the ultrasonic image 302. It is preferable that a region corresponding to the acoustic shadow 307 be extracted based on determination, for example, using CT values of a CT image, and the brightness of an area 308 that is deeper than that region be reduced. Similarly, an area 310 is extracted, using CT values, from a region where a blood vessel exists and the region is displayed, for example, in red, like an ultrasonic CFM (color flow mapping) image 309. This makes it possible to display the reference image 301, which allows easy comparison with the ultrasonic image 302.

Figure 4:
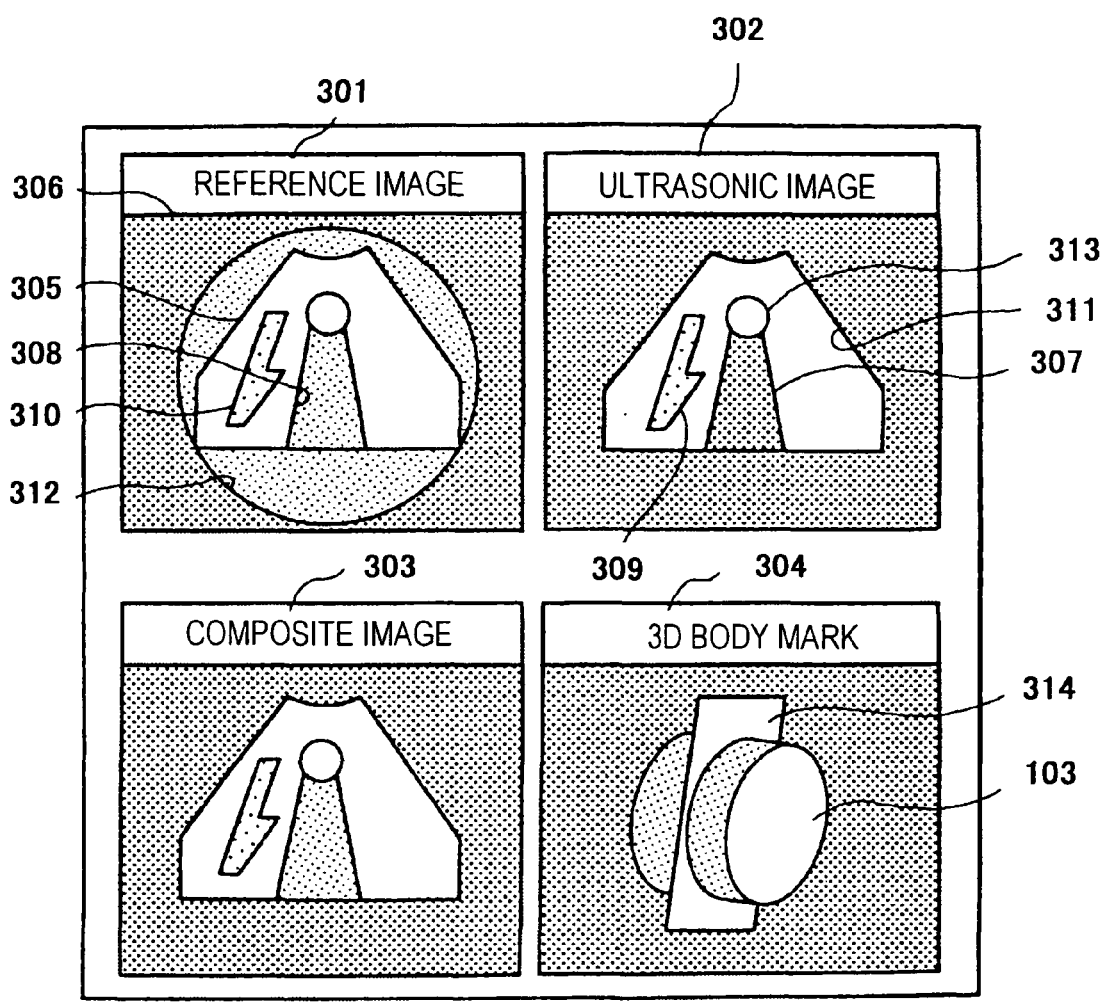
FIG. 4 is a view showing a display example of an ultrasonic image, a reference image, a composite image, and a 3D body mark according to a feature of the present invention.

On the other hand, the 3D body-mark determining unit 112 extracts a three-dimension visualized image, such as a 3D body mark 304 in FIG. 4, by using volume image data, superimposes a scan plane 314 in a translucent color on the three-dimension visualized image, and displays the resulting image. As the three-dimensional visualized image, for example, a known method, such as volume rendering or surface rendering, can be used. Displaying the 3D body mark 304 allows the positional relationship between the patient 103 and the scan plane 314 to be recognized in three dimensions. The 3D body-mark determining unit 112 may be provided with a function for extracting a region of interest, specified by the operator, from the volume image data and determining the distance and the direction from the scan plane to the region of interest.

The adder 113, which provides the image processing means, is intended to determine a composite image 303 of the reference image 301 and the ultrasonic image 302. The adder 113, for example, converts the reference image 301 into a translucent-color image and superimposes it on the ultrasonic image 302. Instead, a difference image between the reference image 301 and the ultrasonic image 302 may be obtained and drawn. This can facilitate that the reference image 301 and the ultrasonic image 302 are compared with each other using one image. With the difference image, for example, when an ultrasonic volume image data obtained in advance is used as the reference image, it is useful to diagnose a temporal change in living-body tissues of the patient.

Thus, as shown in FIG. 4, the ultrasonic image 302, the reference image 301, the composite image 303, and the 3D body-mark 304 of the same cross section are drawn on the monitor 114. This allows the operator to perform effective diagnosis while comparing those images.

For example, using the medical diagnostic imaging apparatus 102 to obtain volume image data centering at a treatment region before medical treatment, causing the ultrasonic diagnosis apparatus 101 to capture an image of the treatment region after the medical treatment, and displaying a reference image before the medical treatment and an ultrasonic image after the medical treatment, for example, in an aligned manner can facilitate determination of the effect of the medical treatment. Also, synthesizing an image of a difference between the reference image before the medical treatment and the ultrasonic image after the medical treatment and displaying the difference image further facilitates the determination of the effect of the medical treatment. In particular, performing display in added color according to the degree of the difference can further facilitate viewing.

By reducing the image size and changing the frame rate, the reference-image determining unit 111 can increase the speed of reconstructing a reference image in accordance with the motion of the probe 104. That is, the reference-image determining unit 111 determines the movement speed and the rotation speed of the scan plane, based on the scan-plane coordinate data. When the speed is greater than a certain threshold, the reference-image determining unit 111 reduces the image size to reconstruct the reference image at a high speed. That is, when the movement of the probe 104 is fast, priority is given to the frame rate over the image quality to draw the reference image at a high speed, and when the movement of the probe 104 is slow, priority is given to the image quality over the frame rate to reconstruct and draw the reference image. This makes it possible to draw the reference image so as to correspond to the ultrasonic image that varies according to the motion of the probe 104.

Figure 5:
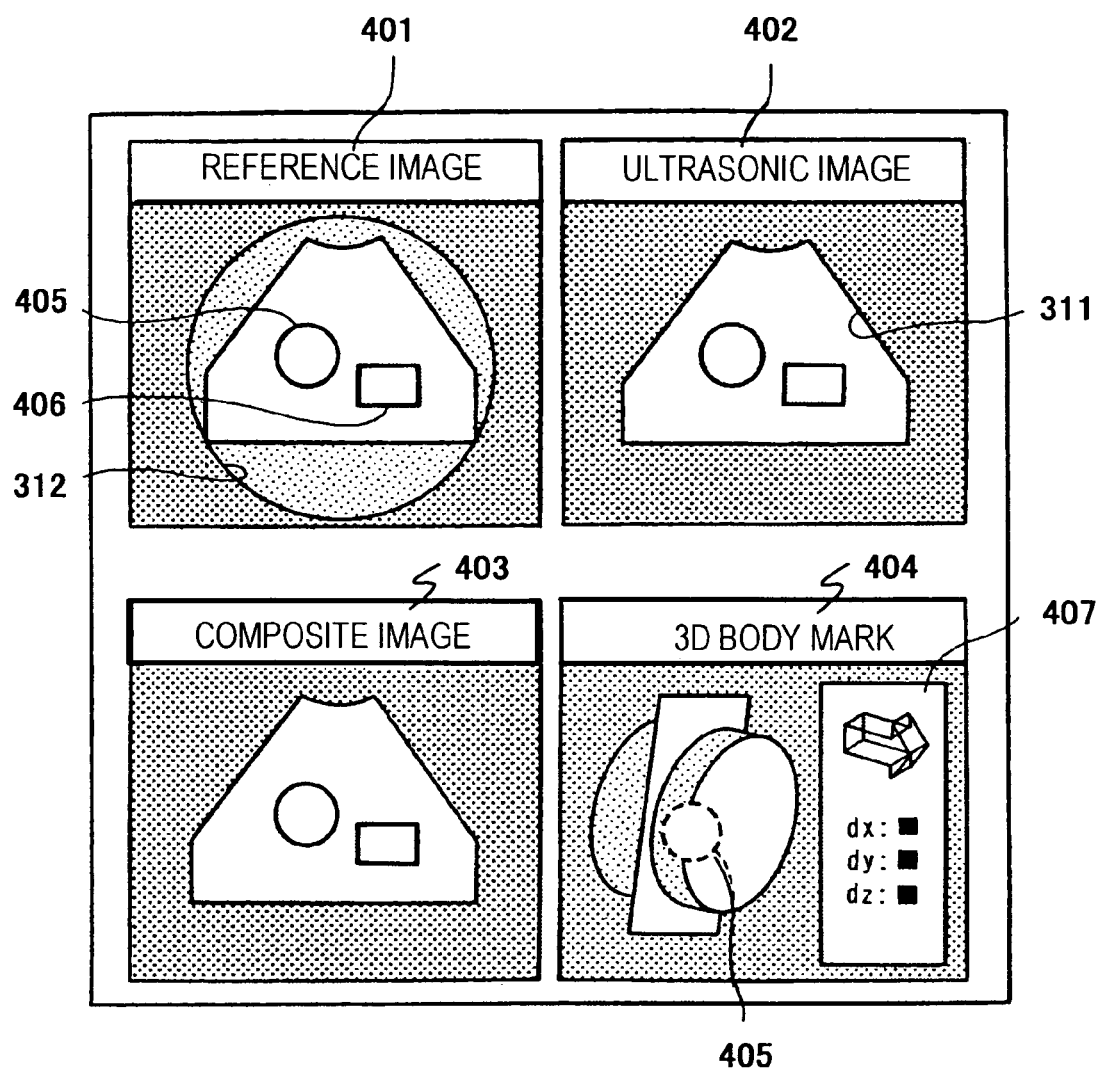
FIG. 5 is a view showing a display example of an ultrasonic image, a reference image, a composite image, and a 3D body mark which are preferable for navigation according to a feature of the present invention.

An image-display processing method with a navigation function will further be described with reference to FIG. 5. This ultrasonic diagnosis apparatus is adapted to allow navigation for guiding the scan plane of the probe 104 to a target 405 that the operator pre-set on a reference image in the volume image data. The target 405 can be set by designating a region with a mouse, for example, on an axial image, sagittal image, coronal image, and three-dimensional visualized image. The 3D body-mark determining unit 112 calculates the distance and direction from the current scan plane to the center of the target 405 and displays a three-dimensional arrow image and numeric values in a display region 407 on the screen of a 3D body mark 404. The boundary of the region of the target 405 is also rendered in a reference image 401 and an ultrasonic image 402. This allows the operator to visually recognize the distance from the current ultrasonic scan plane 314 to the target 405. When the target 405 enters the scan plane 314, a boundary determined from the reference image 401 is also displayed in the ultrasonic image 402. Consequently, it is easy to recognize an association relationship between the reference image 401 and the ultrasonic image 402.

Additionally, a region of interest (ROI) 406 that the operator set on any of the ultrasonic image 402, the reference image 401, and a composite image 403 is displayed on all the images. This facilitates the recognition of an association relationship of the region of interest.

(Third Embodiment)

Figure 6:
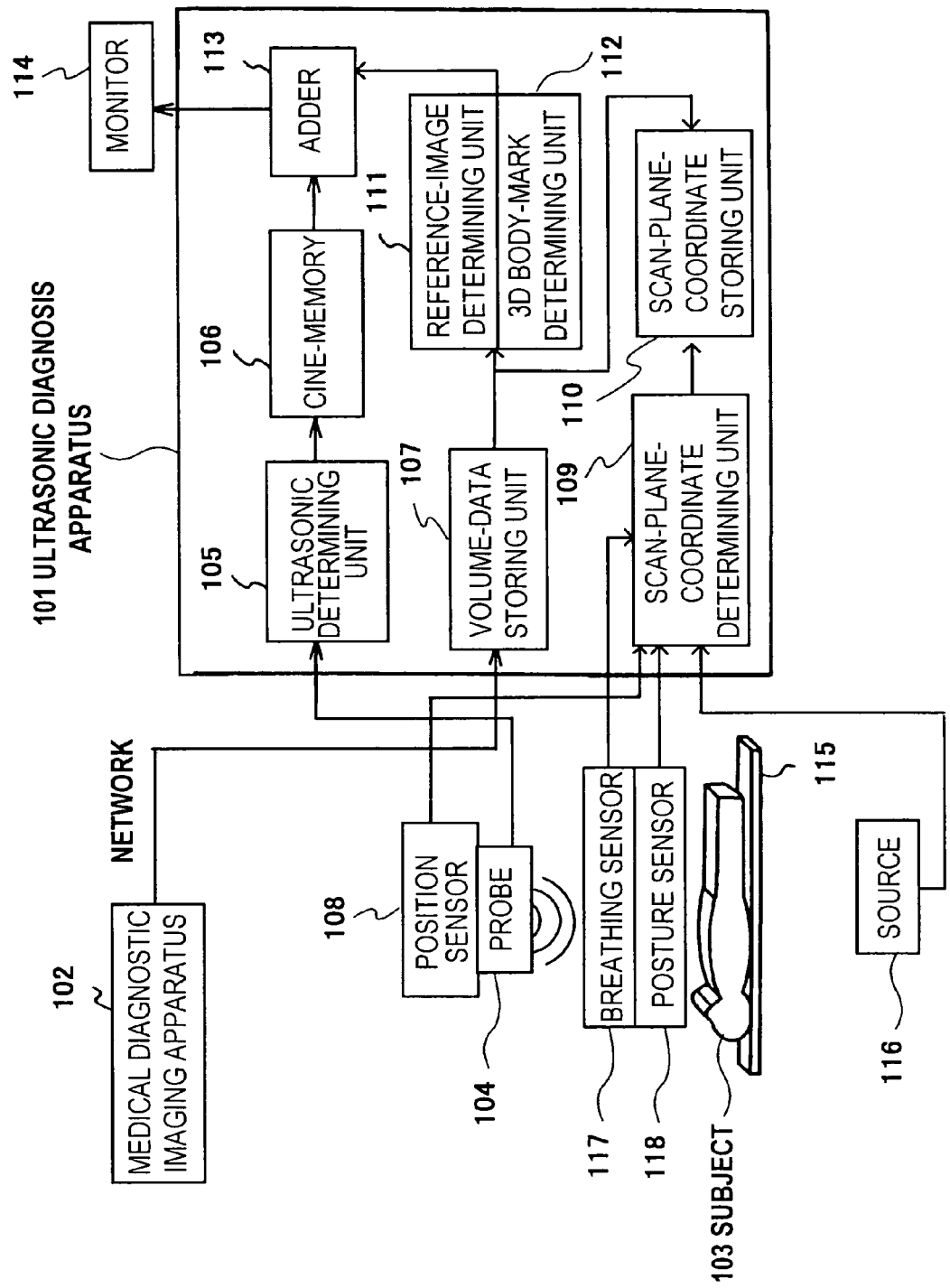
FIG. 6 is a block diagram of a specific diagnostic imaging system to which an ultrasonic diagnosis apparatus of still another embodiment of the present invention is applied.

FIG. 6 shows the configuration of a diagnostic imaging system to which an ultrasonic diagnosis apparatus of another embodiment of the present invention is applied. In FIG. 6, what are different from the embodiment shown in FIG. 2 are that a breathing sensor 117 for detecting the amount of breathing of the patient 103 and a posture sensor 118 for detecting the body movement are provided and outputs of the detections are input to the scan-plane-coordinate determining unit 109. Although processing for associating a volume-imagedata coordinate system with a scan-plane coordinate system was omitted in the embodiment in FIG. 2, details thereof will be described.

Figure 7A:
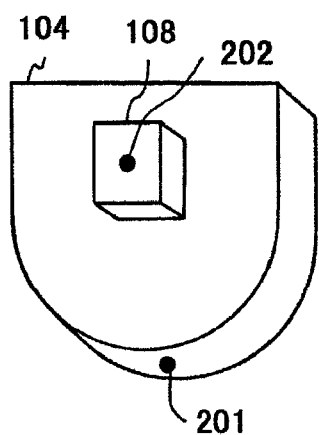
FIG. 7 are block diagrams of a position-sensor-equipped probe in one embodiment according to the present invention.
Figure 7B:
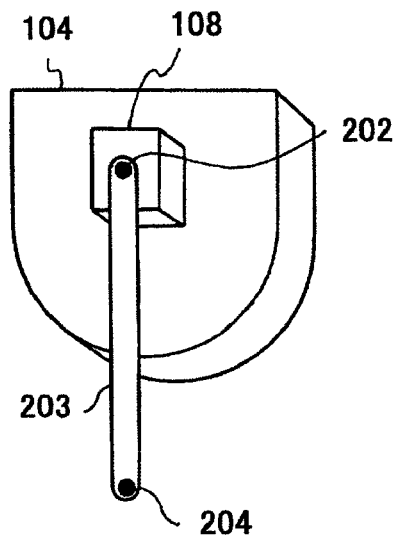

In the present embodiment, as shown in FIG. 7A, the position sensor 108 is attached to one surface of the probe 104 to make it possible to detect the position and inclination of the probe 104, i.e., the position and inclination of the ultrasonic scan plane, in a coordinate system formed by the source 116. In FIG. 7A, transducers are arranged on a circular arc surface of the probe 104 and the distance between a center point 201 of the transducers and a center point 202 of the position sensor 108 has been accurately determined. The relationship between the probe 104 and the position sensor 108 is not limited to what is shown in the figure and can be configured as shown in FIG. 7B. That is, the arrangement can be such that a bar-shaped pointer 203 is detachably attached in association with the position sensor 108 and an end point 204 of the pointer 203 is used as a reference point relative to the center point 202. With this arrangement, the probe 104 of the present embodiment can also be utilized as a pointing device.

Figure 8A:
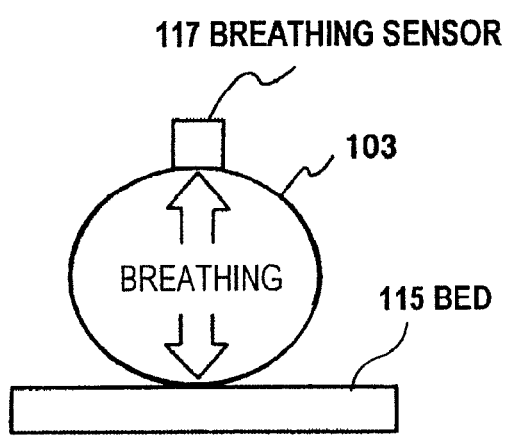
FIG. 8 show the configuration and the processing procedure of breathing-amount determining means according to the present invention.
Figure 8B:
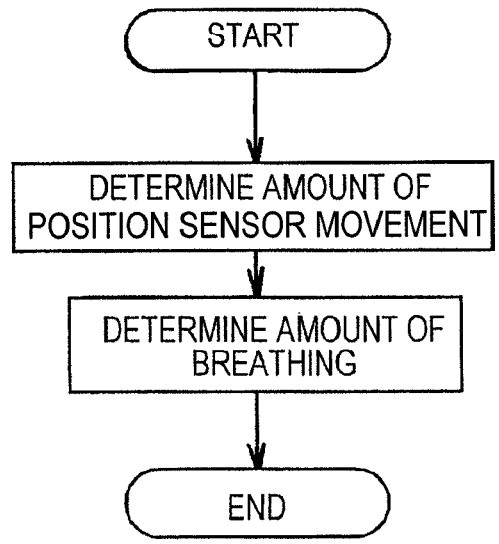

In the same manner as the position sensor 108, the posture sensor 118 is attached to the body surface of the patient 103 so as to measure the position and inclination of the patient 103 in the reference coordinate system formed by the source 116. The breathing sensor 117 measures the amount of breathing of the patient 103. For example, as shown in FIG. 8A, the breathing sensor 117 having a function similar to the position sensor 108 is attached to the body surface of the patient 103, lying on the bed 115, so as to detect the amount of body-surface movement caused by the breathing. As shown in FIG. 8B, the measured amount of movement can be converted into an amount of breathing.

While the scan-plane-coordinate determining unit 109 and the scan-plane-coordinate storing unit 110 are configured to be essentially the same as those in the second embodiment, features and functions according to the present embodiment will be specifically described. The scan-plane-coordinate determining unit 109 has a function for correcting scan-plane coordinates in accordance with the posture information of the patient 103 and the amount of breathing of the patient 103. The scan-plane coordinates as used herein refer to the coordinates of an ultrasonic scan plane imaged by the probe 104. As shown in FIG. 9, the scan-plane-coordinate determining unit 109 and the scan-plane-coordinate storing unit 110 include a scan-plane coordinate-system storing unit 211 a volume-image-data coordinate-system storing unit 212, a posture-change-amount determining unit 213, an internal-organ-movement-amount determining unit 214, a correcting unit 215, and a corrected-scan-plane-coordinate determining unit 216. As in the embodiment shown in FIG. 2, the reference-image determining unit 111 receives the scan-plane coordinates, extracts same-cross-section image data corresponding to the scan-plane coordinates from the volume-data storing unit 107, and reconstructs a reference image. The adder 113 then draws a reference image, output from the reference-image determining unit 111, and an ultrasonic image, read from the cine-memory 106, on the monitor 114. The ultrasonic image and the reference image are typically displayed on the same screen in an aligned manner, but instead, can be displayed in a superimposed manner. When they are displayed in a superimposed manner, it is desired that the reference image be translucent.

Now, processing for associating volume-image-data coordinates with scan-plane coordinates will be described with reference to FIGS. 10, 11, and 12. The coordinate association processing in the present embodiment can be broadly classified into an initialization stage shown in FIG. 10 and a diagnosis stage shown in FIG. 11.

Figure 10:
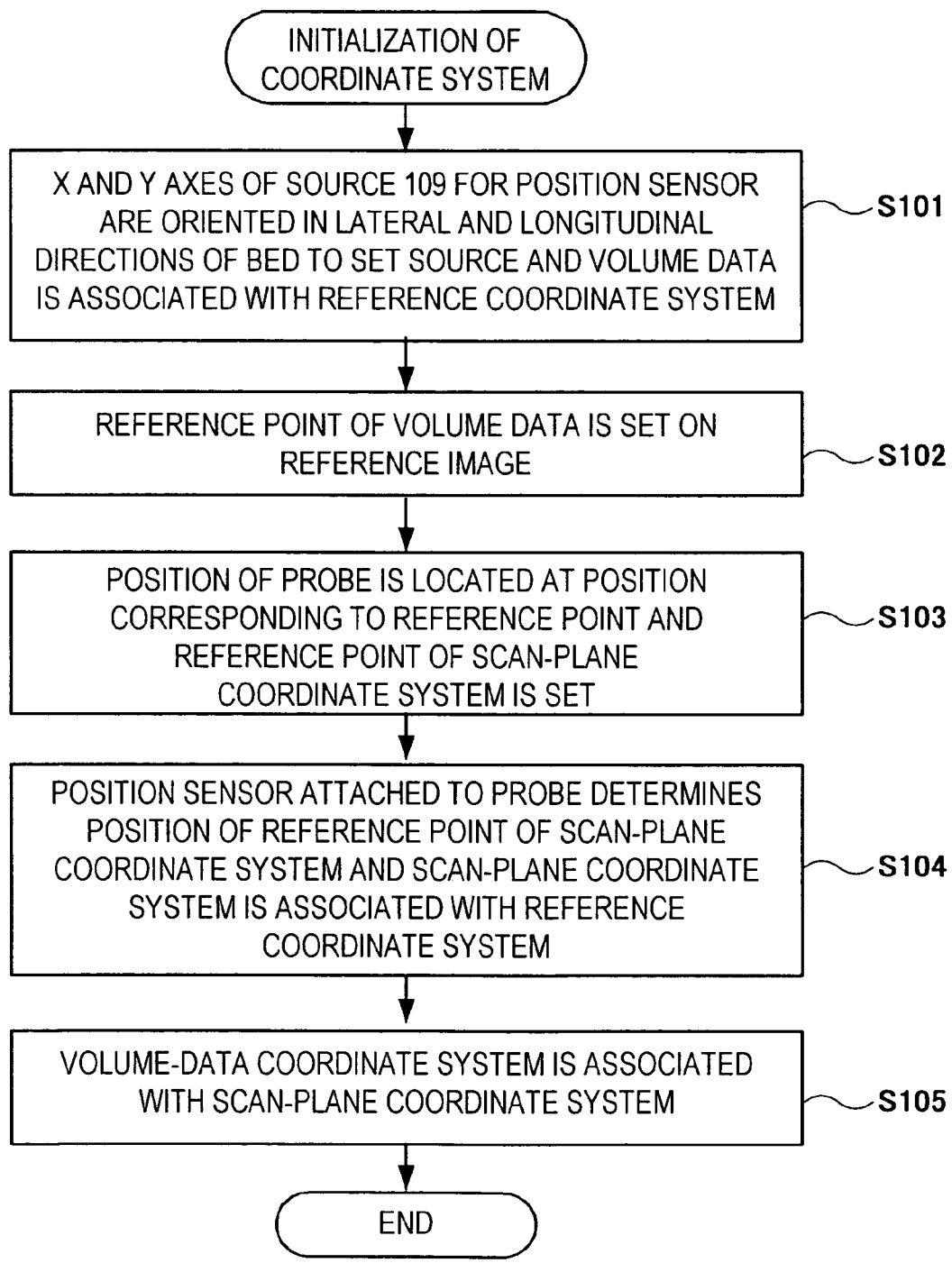
FIG. 10 is a flow chart of initialization processing for coordinate associating processing in the embodiment shown in FIG. 6.

First, a description is given of the initialization stage shown in FIG. 10, i.e., processing during the imaging of volume image data. In step S101, as shown in FIG. 12B, the x axis of the source 116 for the position sensor is oriented in the lateral direction of the bed 115, the y axis is oriented in the longitudinal direction of the bed 115, and the z axis is oriented in the vertical direction of the bed 115 to thereby place the source. Thus, the x, y, and z axes of a source coordinate system that has the origin at, for example, a center 224 of the source 116 are aligned parallel to the x, y, and z axes of a coordinate system having an original 225 at one corner of volume image data shown in FIG. 12A. That is, volume data 221 shown in FIG. 12A is obtained by typically laying the patient 103 on the bed 115 and capturing a tomographic image perpendicular to the body axis (the y-axis direction) of the patient 103. Placing the source 116 so as to be aligned with the bed 115 allows the x, y, and z axes of the reference coordinate system of the source 116 and the coordinate system of the volume data 221 to be substantially parallel to each other.

Next, in step S102, a reference point 223 is set in the volume data 221. The reference point 223 is set on an operation screen by using a pointing device, such as a mouse. The operation screen is displayed with a reference image obtained by imaging volume image data. The operation screen may include an axial image, sagittal image, coronal image, or three-dimensional visualized image. Designating the reference point 223 on any of the images makes it possible to set the reference point 223 on the body surface or inside the body in the volume image data.

In contrast, in step S103, a reference point 222 in the scan-plane coordinate system is set, for example, by locating the probe 104 with the position sensor 108 at a position corresponding to the reference point 223 of the volume data 221 and holding the probe 104. For example, when the reference point 222 of the volume data is designated on the body surface, the contact point 201 of the probe 104 is placed at a body-surface position of the actual patient 103, the body-surface position corresponding to the reference point 222, to set the reference point 222 in the scan-plane coordinate system. In this case, since the position of the reference point 222 and the position of the reference point 223 match each other, it is possible to match the coordinate system of the volume image data and the coordinate system of the scan plane. In this case, the probe 104 is used as a pointing device. Here, in order to facilitate the work of placing the probe at the body-surface position of the actual patient, the body-surface position being corresponding to the position of the reference point specified in the volume image data, it is preferable that a distinctive point (e.g., a xiphoid process or a blood vessel branch) that can be easily found on the body surface from the external view be selected as the reference point 223 specified in the volume image data.

On the other hand, when the reference point in the volume image data is specified inside the body, the probe is manipulated, an ultrasonic image containing a region containing the in-vivo reference image 223 is displayed, and a region corresponding to the in-vivo reference point 223 is specified on the ultrasonic image by using a pointing device, such as a mouse. Then, the distance between the specified point and the center 202 or the contact point 201 of the probe 104 is determined and the coordinates of the two reference points 222 and 223 are associated with each other. In this case, in order to easily identify the in-vivo reference point 223 on the ultrasonic image, it is preferable that an easy-to-find distinctive point on the ultrasonic image be selected as the reference point specified in the volume image data, as described above.

Next, in step S104, relationship data for associating the scan-plane coordinate system with the reference coordinate system of the source 116 is determined. First, the origin of the patient 103 in the real space is set at the reference point 222. The coordinate axes of the scan plane coordinate system are set parallel to the coordinate axes of the source coordinate system. Then, the position (X, Y, and Z) of the reference point 222 of the probe 104, the position being detected by the position sensor 108, is determined, the scan-plane coordinate system and the source coordinate system are associated with each other, and the resulting association data is stored in the scan-plane coordinate-system storing unit 211 shown in FIG. 9. In this manner, the volume-image-data coordinate system and the scan-plane coordinate system can be associated with each other via the reference coordinate system of the source 116. In step S105, data for associating the volume-image-data coordinate system with the scan-plane coordinate system is created and is stored in the volume-image-data coordinate-system storing unit 212 shown in FIG. 9.

Since the source 116 is placed in step S101 such that the coordinate axes of the volume-image-data coordinate system are parallel to the coordinate axes of the source coordinate system. Setting only one reference point 223 in the volume-image-data coordinate system can facilitate that those two coordinate systems are associated. That is, placing the source 116 in an appropriate direction according to the direction of the body axis of the patient can readily align the coordinate systems. However, in the present invention, three reference points 223 can also be set. In this case, the accuracy of associating the coordinate systems can be improved. For example, when the coordinate systems are determined with three reference points, one of the three points is designated as the origin of the coordinate system, vectors from the origin to the remaining two points are designated as an X axis and a Y axis, and an axis perpendicular to the x and y axes is designated as a Z axis to thereby achieve the alignment. This makes it possible to associate the coordinate systems without caring about the direction of the placed source 116. The remaining two points can be automatically set on the screen by causing a measurement tool for performing measurement on image data to perform the above-described processing.

The association data between the volume-image-data coordinate system and the scan-plate coordinate system, the association data being created as described above, is used during ultrasonic diagnosis to determine scan-plane coordinates according to a procedure shown in FIG. 11. The scan-plane-coordinate determining unit 109 determines the scan plane coordinates, in accordance with the position and inclination of the probe 104 which are detected by the position sensor 108 attached to the probe 104 (step S106). Next, the reference-image determining unit 111 cuts a reference image, corresponding to the scan-plane coordinates, out from the volume image data and causes the reference image to be displayed on the monitor 114 via the adder 113 (step S107). This allows the operator to draw a reference image that matches an ultrasonic image corresponding to an arbitrary set position and direction of the probe, thereby improving the accuracy of diagnosis.

Next, a feature and a function of the present embodiment for correcting the scan plane coordinates in accordance with a change in the posture and so on will be described. That is, as diagnosis proceeds, a displacement may occur between the coordinate systems of the volume image data and the scan plane, due to factors, such as a change in the posture of the patient and internal-organ movement caused by the breathing of the patient. Such a displacement may make it impossible to draw a reference image that matches the ultrasonic scan plane. Accordingly, in the present embodiment, in a diagnosis stage, the scan plane-coordinate determining unit 109 is adapted to correct a displacement in the scan-plane coordinate system.

Correction for a change in the posture of the patient will be described first. The posture of the patient can be detected with the posture sensor 118 shown in FIG. 6. Thus, a difference between the posture during initialization and the posture during diagnosis is determined by the posture-change-amount determining unit 213, and in accordance with difference, the scan-plane coordinate system is shifted and rotated to perform correction.

Next, means for correcting a coordinate-system displacement due to internal-organ movement caused by the breathing of the patient will be described with reference to FIG. 13. The operator performs this correction processing, while viewing a rendered reference image and ultrasonic image. The operator first pays attention to the reference image. The operator displays, for example, a distinctive cross section, including the patient' blood vessel such as a portal vein or superior mesenteric artery, and performs freezing, while manipulating the probe 104 (step S201). Next, the operator pays attention to the ultrasonic image, and renders the same cross section as the frozen image of the reference image and performs adjustment, while performing visual comparison with the frozen image (step S202). Here, a difference (the amount of change) between the scan-plane coordinates during the freezing and the scan plane-coordinates during the adjustment corresponds to the amount of internal-organ movement. Thus, the scan-plane-coordinate determining unit 109 determines a difference (the amount of change) between the scan-plane coordinates during the freezing and the scan-plane coordinates during the adjustment (step S203). The scan-plane coordinate system is shifted and rotated by an amount corresponding to the difference to thereby perform correction (step S204). Consequently, even when the depth of breathing of the patient differs from that in the initialization stage, the scan-plane coordinates and the volume-image-date coordinate system can be correctly associated with each other.

Figure 13:
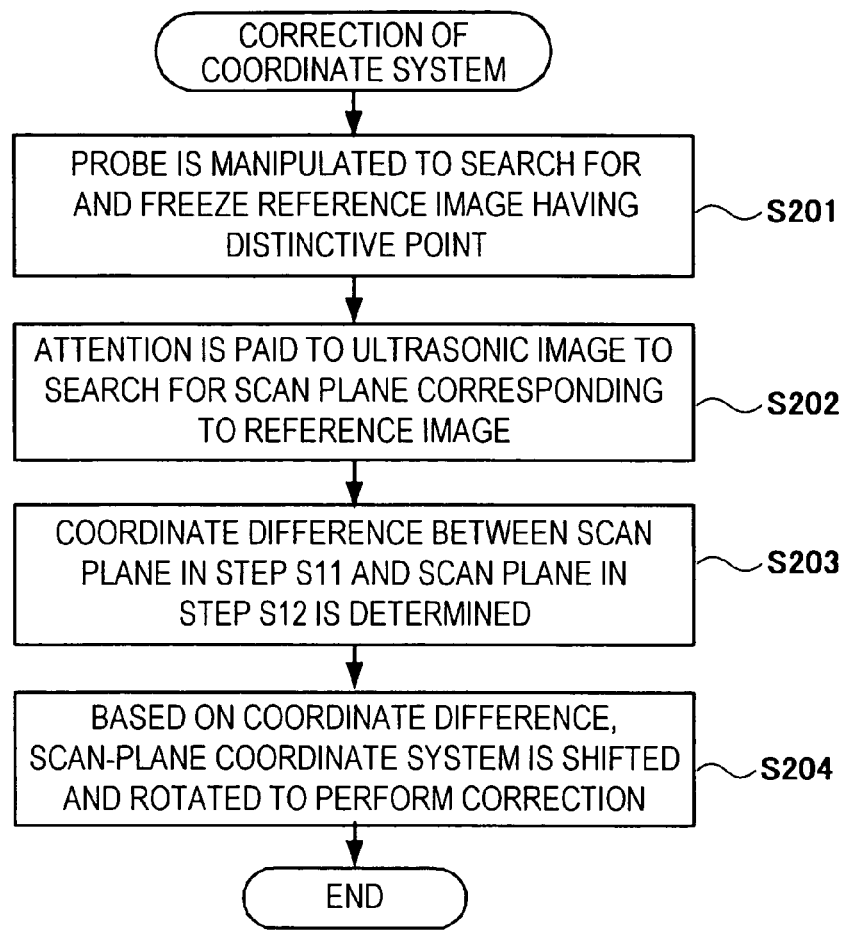
FIG. 13 is a flow chart of one embodiment for correcting a reference-coordinate-system displacement caused by breathing or the like of a patient.
Figure 14:
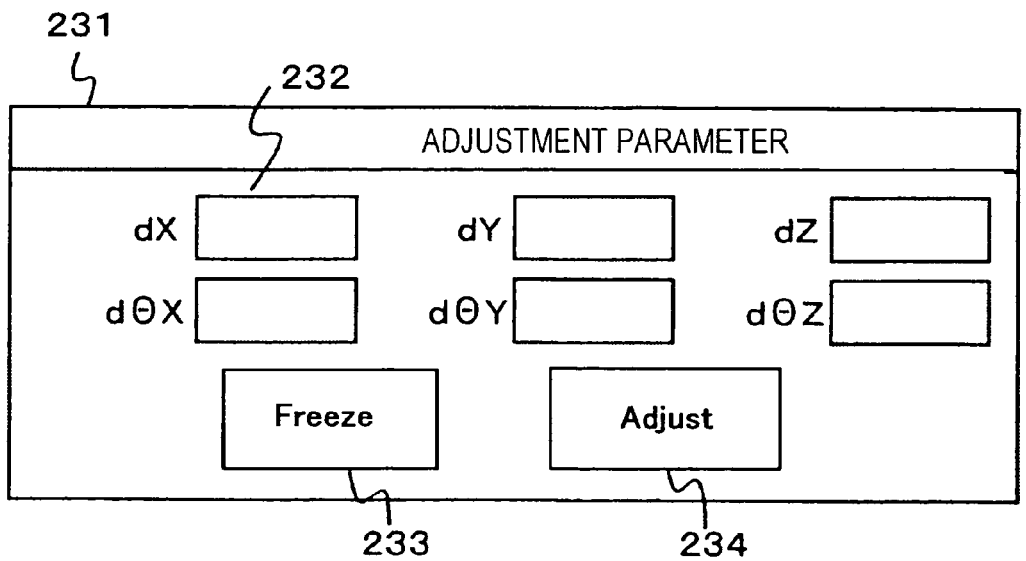
FIG. 14 shows one example of a coordinate adjustment screen for assisting processing for correcting scan plane coordinates.

During the correction processing in FIG. 13, a coordinate adjustment screen 231 shown in FIG. 14 is displayed so as to allow a freeze key 232 and an adjust key 234 to be operated on the screen. Also, the amount of movement and the amount of rotation which are related to the correction can also be displayed in parameter edit boxes 232. The operator can perform correction by directly inputting numeric values to the edit boxes 232.

In addition, an input amount of breathing is measured by the breathing sensor 117, the correction is repeated at multiple depths of breathing, and the correlation between the amount of breathing and the amount of internal-organ movement is determined. With this approach, a displacement caused by internal-organ movement can be automatically corrected in accordance with an input from the breathing sensor.

Hereinabove, a volume-image-data reference image having a distinctive point is frozen and an ultrasonic scan plate corresponding to the reference image has been determined. Conversely, the arrangement may also be such that an ultrasonic scan plane having a distinctive point is frozen and image processing is performed to automatically determine a reference image corresponding to the ultrasonic scan plane. Specifically, an ultrasonic scan plane displaying a distinctive point of the patient is frozen and the ultrasonic scan plane is recorded in a storage medium, such as the cine-memory 106. By using a known pattern matching method, the reference-image determining unit 111 extracts a reference image corresponding to the distinctive point of the frozen ultrasonic scan plane from the volume image data stored in the volume-data storing unit 107. The reference image extracted as a result of matching is displayed on the monitor 114. In the reference-image matching processing, there is no need to search all the volume image data. Thus, only data regarding the scan-plane side, viewed in the scan direction of the ultrasonic probe 104, may be extracted to match distinctive regions. Magnification may also be adjusted such that a distinctive point on the ultrasonic scan plane and a distinctive point on the reference image have the same magnification. In this manner, extracting a reference image from image information having a distinctive point can enhance the accuracy of aligning the ultrasonic scan plane and the reference image.

In addition, another example of the means for correcting a coordinate-system displacement due to internal-organ movement caused by the breathing of the patient will be described with reference to FIG. 15. As in the case of FIG. 13, the operator performs this correction processing while viewing a rendered reference image and an ultrasonic image. First, the probe 104 is placed on the patient so that cross sections perpendicular to a direction in which the internal organs move due to breathing are displayed. The direction in which the internal organs move due to breathing is typically the body axis direction of the patient. The probe 104 placed on the patient is then moved in the internal-organ movement direction, and distinctive ultrasonic tomographic images, including a blood vessel such a portal vein or superior mesenteric artery, are rendered. At this point, due to the occurrence of a displacement between the volume-image-data coordinate system and the scan-plate coordinate system, a cross-section displacement in the body axis direction occurs between the ultrasonic image and the reference image. In this state, the ultrasonic image and the reference image are frozen, cine playback is performed, and the operator specifies a corresponding combination of a reference image and an ultrasonic image. For example, in the example shown in FIG. 15, since blood vessels can be most clearly rendered on a reference image 1 displayed at time t1 and an ultrasonic image 2 displayed at time t2, it is determined that they are corresponding images. It can be understood from this that, although the reference image 1 corresponding to the ultrasonic image 2 is supposed to be displayed at the position of time t2, the corresponding reference image is displayed at time t1. At this point, a difference (the amount of change) between scan-plane coordinates 1 and scan-plane coordinates 2 which are stored in the scan-plane-coordinate storing unit 110 corresponds to the amount of internal-organ movement. Accordingly, determining the difference between the scan-plane coordinates 1 and the scan-plane coordinates 2 and correcting the scan plane coordinates makes it possible to correct a coordinate-system displacement caused by the internal-organ movement.

The invention claimed is:

1. An ultrasonic diagnosis apparatus comprising:
   an ultrasonic image generating unit configured to generate an ultrasonic tomographic image on a scan plane of an ultrasonic wave from reflection echo signals output from an ultrasonic probe;
   a storage unit configured to store volume image data pre-obtained by a diagnostic imaging apparatus;
   a reference-image generating unit configured to extract reference tomographic image data corresponding to the ultrasonic tomographic image from the volume image data stored in the storage unit and generate a tomographic reference image;
   a cine-memory configured to store the ultrasonic tomographic image generated by the ultrasonic-image generating unit;
   a position sensor configured to detect a position and an inclination of the ultrasonic probe;
   a coordinate determining unit configured to determine scan-plane-coordinate data of the ultrasonic tomographic image in accordance with an output from the position sensor;
   a scan-plane-coordinate-system storing unit configured to store the determined scan-plane-coordinate data;
   a controller configured to cause the tomographic reference image and the ultrasonic tomographic image to be displayed on a screen; and
   a display unit configured to display the reference image and the ultrasonic tomographic image;
   wherein:
      an image processing unit reads the ultrasonic tomographic image from the cine-memory and causes the reference tomographic image corresponding to the read ultrasonic tomographic image to be displayed, the reference image being output from the reference-image generating unit,
      cine playback of the ultrasound tomographic image is executed by referring to ultrasonic tomographic image data stored in the cine-memory, and cine playback of the reference tomographic image is executed by using the scan-plane coordinate data stored in the scan-plane-coordinate storing unit, and
      the ultrasonic tomographic image data and the scan-plane coordinate data are stored in synchronization with each other.

2. The ultrasonic diagnosis apparatus according to claim 1, further comprising:
   at least one of a posture sensor configured to detect a change in the posture of the patient and a sensor for detecting breathing; and
   a correcting unit configured to correct the scan-plane-coordinate data in accordance with an amount of internal-organ movement caused by a posture change or the breathing of the patient during ultrasonic diagnosis.

3. The ultrasonic diagnosis apparatus according to claim 1, further comprising:
   a scan-plane-coordinate determining unit configured to determine scan-plane-coordinate of an ultrasonic tomographic image captured by the ultrasonic probe, in association with a reference coordinate system; and
   a volume-data-coordinate determining unit configured to determine tomographic-plane coordinates associated with the scan-plane coordinate data, based on the volume image data obtained in association with the reference coordinate system,
   wherein the reference-image generating unit reads the tomographic-plane coordinates, associated with the coordinates determined by the scan-plane-coordinate determining unit, from the volume-data-coordinate storing unit and extracts the reference image.

4. An ultrasonic diagnosis apparatus comprising:
   an ultrasonic image generating unit configured to generate an ultrasonic tomographic image on a scan plane of an ultrasonic wave from reflection echo signals output from an ultrasonic probe;
   a storage unit configured to store volume image data pre-obtained by a diagnostic imaging apparatus;
   a reference-image generating unit configured to extract reference tomographic image data corresponding to the ultrasonic tomographic images from the volume image data stored in the storage unit and generate a tomographic reference image;

a position sensor configured to detect a position and an inclination of the ultrasonic probe in association with a reference coordinate system;

a coordinate determining unit configured to determine scan-plane-coordinate data of an ultrasonic tomographic image captured by the ultrasonic probe in association with the reference coordinate system, in accordance with an output from the position sensor;

a reference-point inputting unit configured to set a reference point on a reference tomographic image displayed on the screen based on the volume image data obtained in association with the reference coordinate system;

a volume-data-coordinate determining unit configured to determine coordinates of the volume image data associated with the scan-plane-coordinate data, by determining a coordinate relationship between the reference point on the reference tomographic image and a point on the ultrasonic tomographic image obtained by bringing the ultrasonic probe in contact with a body surface of the patient;

a controller configured to cause the tomographic reference image and the ultrasonic tomographic image to be displayed on the screen; and a display unit configured to display the reference image and the ultrasonic tomographic image, wherein:
the reference-image generating unit reads the coordinates of the volume image data, associated with the scan-plane-coordinate data determined by the scan-plane-coordinate determining unit, and the reference-image generating unit extracts reference tomographic image data of a portion corresponding to a same view area of the ultrasonic tomographic image to generate the reference tomographic image, in accordance with the coordinates of the volume image data, cine playback of the ultrasonic tomographic image is executed by referring to ultrasonic tomographic image data, and cine playback of the reference tomographic image is executed by using the scan-plane coordinate data, and the ultrasonic tomographic image data and the scan-plane coordinate data are stored in synchronization with each other.

5. The ultrasonic diagnosis apparatus according to claim 4, further comprising:
at least one of a posture sensor configured to detect a change in the posture of the patient and a sensor for detecting breathing; and
a correcting unit configured to correct the scan-plane-coordinate data in accordance with an amount of internal-organ movement caused by a posture change or the breathing of the patient during ultrasonic diagnosis.

6. The ultrasonic diagnosis apparatus according to claim 1, wherein an ultrasonic-image processing sequence is configured to be synchronized with a reference-image processing sequence in terms of starting and freezing.

7. The ultrasonic diagnosis apparatus according to claim 1, wherein the position sensor is configured to obtain the position and the inclination of the ultrasonic probe in synchronization with a transmission/reception of the ultrasonic wave.

8. The ultrasonic diagnosis apparatus according to claim 1, wherein the coordinate determining unit is configured to determine the scan-plane-coordinate data in synchronization with generating the ultrasonic tomographic image.

9. The ultrasonic diagnosis apparatus according to claim 1, wherein the coordinate-system storing unit is configured to store the determined scan-plane-coordinate data in synchronization with storing the generated ultrasonic tomographic image in the cine-memory.

10. The ultrasonic diagnosis apparatus according to claim 1, wherein the position sensor is configured to obtain to the position and the inclination of the ultrasonic probe in synchronization with a transmission/reception of the ultrasonic wave.

11. An ultrasonic diagnosis method comprising:
generating an ultrasonic tomographic image on a scan plane of an ultrasonic wave from reflection echo signals output from an ultrasonic probe;
storing volume image data pre-obtained by a diagnostic imaging apparatus;
extracting reference tomographic image data corresponding to the ultrasonic tomographic image from the stored volume image data;
generating a reference tomographic image;
storing the generated ultrasonic tomographic image;
detecting a position and an inclination of the ultrasonic probe;
determining scan-plane-coordinate data of the ultrasonic tomographic image in accordance with the position and the inclination of the ultrasonic probe;
storing the determined scan-plane-coordinate data;
causing the reference tomographic image and the ultrasonic tomographic image to be displayed on a screen; and
displaying the reference image and the ultrasonic tomographic image, wherein:
the scan-plane-coordinate data of the ultrasonic tomographic image is read;
the reference tomographic-image data corresponding to the read scan-plane-coordinate data is read from the volume image data,
the reference tomographic image is generated;
the ultrasonic tomographic image is read,
the reference tomographic image corresponding to the read ultrasonic tomographic image is caused to be displayed,
cine playback of the ultrasonic tomographic image is executed by referring to ultrasonic tomographic image data, and cine playback of the reference tomographic image is executed by using the scan-plane coordinate data, and
the ultrasonic tomographic image data and the scan-plane coordinate data are stored in synchronization with each other.

12. An ultrasonic diagnosis method comprising:
generating an ultrasonic tomographic image on a scan plane of an ultrasonic wave form reflection echo signals output from an ultrasonic probe;
storing volume image data pre-obtained by a diagnostic imaging apparatus;
extracting reference tomographic image data corresponding to the ultrasonic tomographic image from the stored volume image data;
generating a tomographic reference image;
detecting a position and an inclination of the ultrasonic probe in association with a reference coordinate system;
determining scan-plane-coordinate data of the ultrasonic tomographic image captured by the ultrasonic probe in association with the reference coordinate system, in accordance with the position and the inclination of the ultrasonic probe;

setting a reference point on a reference tomographic image displayed on the screen based on the volume image data obtained in association with the reference coordinate system;

determining coordinates of the volume image data associated with the scan-plane-coordinate data, by determining a coordinate relationship between the reference point on the reference tomographic image and a point on the ultrasonic tomographic image obtained by bringing the ultrasonic probe in contact with a body surface of the patient;

causing the tomographic reference image and the ultrasonic tomographic image to be displayed on a screen; and displaying the reference image and the ultrasonic tomographic image, wherein:
  the coordinates of the volume image data associated with the determined scan-plane-coordinate data is read,
  reference tomographic image data of a portion corresponding to a same view area of the ultrasonic tomographic image is extracted to generate the reference tomographic image, in accordance with the coordinates of the volume image data,
  cine playback of the ultrasonic tomographic image is executed by referring to ultrasonic tomographic image data, and cine playback of the reference tomographic image is executed by using the scan-plane coordinate data, and
  the ultrasonic tomographic image data and the scan-plane coordinate data are stored in synchronization with each other.

* * * * *